US00PP33990P2

(12) United States Plant Patent
Probst

(10) Patent No.: US PP33,990 P2
(45) Date of Patent: Mar. 1, 2022

(54) ***COREOPSIS* PLANT NAMED 'IRON LADY'**

(50) Latin Name: ***Coreopsis* hybrid**
Varietal Denomination: Iron Lady

(71) Applicant: Darrell Probst, Hubbardston, MA (US)

(72) Inventor: Darrell Probst, Hubbardston, MA (US)

( * ) Notice: Subject to any disclaimer, the term of this patent is extended or adjusted under 35 U.S.C. 154(b) by 0 days.

(21) Appl. No.: 17/327,886

(22) Filed: May 24, 2021

(51) Int. Cl.
*A01H 5/02* (2018.01)
*A01H 6/14* (2018.01)

(52) U.S. Cl.
USPC ..... Plt./417

(58) Field of Classification Search
USPC ..... Plt./263.1, 417
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of hybrid *Coreopsis* plant named 'Iron Lady' that is characterized by its compact, densely bushy plant habit reaching an average of 35 cm in height and 50 cm in width, its a floriferous and long blooming season of its nearly sterile inflorescences that do not require deadheading; bloom commences in late-June and lasts until frost in Kensington, Conn., its medium sized inflorescences with ray florets that are light yellow in color and flushed with red at the base, its flower intitiation without the need for vernalization, its resistance to powdery mildew and leafspot, and its cold hardiness at least to U.S.D.A. Zone 5.

2 Drawing Sheets

Botanical classification: *Coreopsis* hybrid.
Variety denomination: 'Iron Lady'.

BACKGROUND OF THE INVENTION

The present invention relates to a new and distinct cultivar of *Coreopsis* plant, botanically of hybrid origin and known as *Coreopsis* 'Iron Lady' and will be referred to hereinafter by its cultivar name, 'Iron Lady'. The new cultivar of *Coreopsis* is an herbaceous perennial grown for landscape and container use.

The new Invention arose from an ongoing controlled breeding program in New Braintree, Mass. The objective of the breeding program is to develop hybrid cultivars of *Coreopsis* with unique and superior garden attributes. In particular, to develop cultivars that are long-lived, sturdy, exhibit a true perennial habit and cold hardy to at least U.S.D.A. Zone 5 in a wide range of flower colors and plant forms on plants that do not require vernalization to initiate flowering.

The Inventor made a controlled cross in August of 2014 in New Braintree, Mass. between an unnamed and unpatented proprietary plant from his breeding program as the female parent (ref. code G 08-8) and pollen that was pooled from a variety of unnamed and unpatented proprietary plants from his breeding program as the male parent. The exact characteristics of the pollen parent are therefore unknown. 'Iron Lady' was selected in September of 2015 as a single unique plant amongst the resulting seedlings.

Asexual propagation of the new cultivar was first accomplished by stem cuttings under the direction of the Inventor in Kensington, Conn. in September of 2015. Asexual propagation by stem cuttings has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Iron Lady' as a unique cultivar of *Coreopsis*.

1. 'Iron Lady' exhibits a compact, densely bushy plant habit reaching an average of 35 cm in height and 50 cm in width.
2. 'Iron Lady' exhibits a floriferous and long blooming season of its nearly sterile inflorescences that do not require deadheading; bloom commences in late-June and lasts until frost in Kensington, Conn.
3. 'Iron Lady' exhibits medium sized inflorescences with ray florets that are light yellow in color and flushed with red at the base.
4. 'Iron Lady' exhibits flower intitiation without the need for vernalization.
5. 'Iron Lady' exhibits resistance to powdery mildew and leafspot.
6. 'Iron Lady' exhibits cold hardiness at least to U.S.D.A. Zone 5.

The female parent of 'Iron Lady' differs from 'Iron Lady' in having fertile inflorescences with smaller ray florets that are solid yellow in color. 'Iron Lady' can be most closely compared to *Coreopsis* cultivars 'Lauren' (U.S. Plant Pat. No. 25,592) and 'Enchanted Eve' (U.S. Plant Pat. No. 27,857). 'Lauren' is similar to 'Iron Lady' in having ray florets that are yellow in color, cold hardiness to at least U.S.D.A. Zone 5, and in not requiring vernalization to initiate flowering. 'Lauren' differs from 'Iron Lady' in having inflorescences with ray florets that are solid yellow in color without being flushed red at the base. 'Enchanted Eve' is similar to 'Iron Lady' in having inflorescences with ray florets that are yellow in color with a red base, a compact plant habit, resistance to powdery mildew, cold hardiness to at least U.S.D.A. Zone 5, and in not requiring vernalization to initiate flowering. 'Enchanted Eve' differs from 'Iron Lady' in having inflorescences with ray florets that have a two-toned red eye (base) color that expands in cooler temperatures to cover most of the ray floret surface.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Publications include but are not limited to listings on websites by Wayside Gardens, Jackson and Perkins, Lowey's Greenhouse, James Greenhouse, GL Plants, Vanstone Nurseries, Greenhouse Grower, Gro 'n Sell, Wisconsin Hardy Plant Society, Turks Greenhouses, Gardenzia, Colorado State University, BFG Supply, and Onava.

BRIEF DESCRIPTION OF THE DRAWINGS

The accompanying colored photographs illustrate the overall appearance and distinct characteristics of the new *Coreopsis*. The photographs were taken of a 3-month-old plant of 'Iron Lady' as grown outdoors in a one-gallon container in Encinitas, Calif.

The photograph in FIG. 1 provides a side view of 'Iron Lady' and shows the plant habit in bloom.

Figure 1:
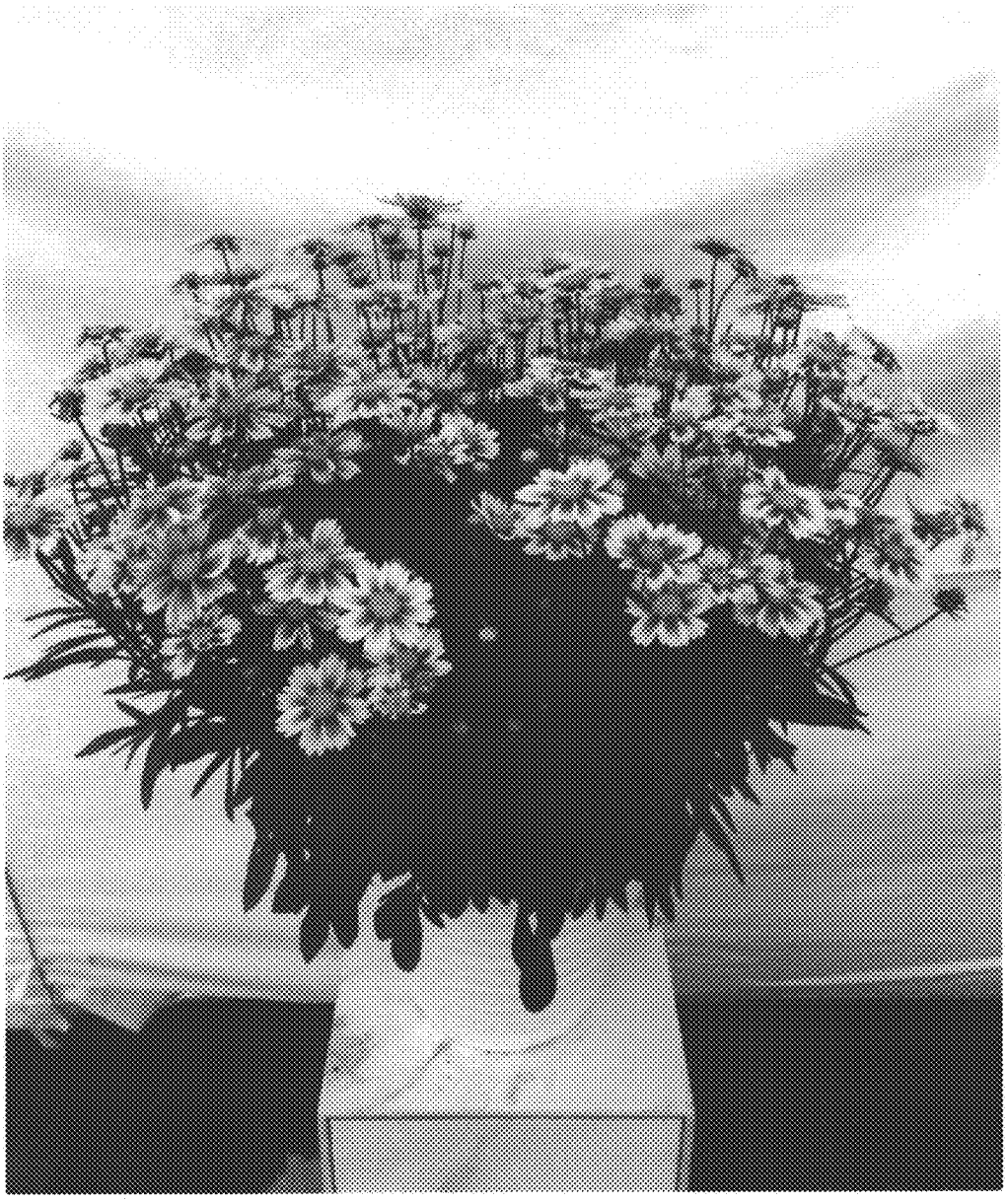
Figure 2:
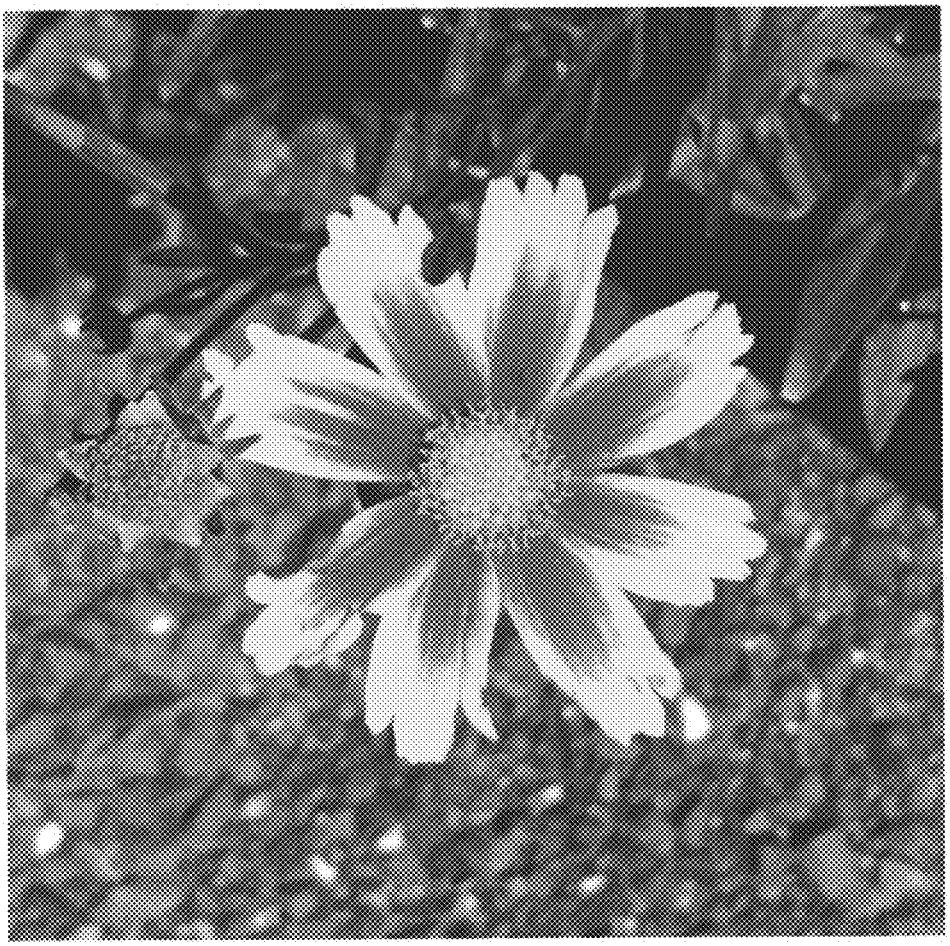

The photograph in FIG. 2 provides a close-up view of an inflorescence of 'Iron Lady'.

The colors in the photographs are as close as possible with the photographic and printing technology utilized and the color values cited in the detailed botanical description accurately describe the colors of the new *Coreopsis*.

DETAILED BOTANICAL DESCRIPTION

The following is a detailed description of 3-month-old plants of 'Iron Lady' as grown outdoors in one-gallon containers in Belchertown, Mass. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Blooms from late-June until frost in Kensington, Conn.

*Plant type*.—Herbaceous perennial.

*Plant habit*.—Clump-forming, bushy and compact, upright leafy flowering stems with inflorescences held above the foliage.

*Height and spread*.—Reaches an average of 35 cm in height and 50 cm in width as grown in a one-gallon container.

*Cold hardiness*.—At least to U.S.D.A Zone 5.

*Diseases and pests*.—Resistance to powdery mildew (*Podosphaera macularis*) and leafspot (*Pseudomonas cichorii*).

*Root description*.—Fibrous and fine, NN155A in color.

*Propagation*.—Stem cuttings.

*Time required for root initiation*.—An average of 10 days for root initiation.

*Growth rate*.—Vigorous, but stays densely compact.

Stem description:

*Shape*.—Flattened, solid.

*Stem color*.—139A and 139B.

*Stem strength*.—Strong.

*Stem size*.—Main stems; an average of 25 cm in length and 5 mm in width, lateral stems; an average of 6 cm in length (excluding peduncles) and 3 mm in width.

*Stem surface*.—Moderately glossy, vertically ridged surface, moderately covered with villous hairs up to 2 mm in length, NN155C in color, slightly transluscent.

*Branching habit*.—Freely branched, an average of 30 basal main stems, lateral stems typically branched as oppositely arranged pairs at each node.

*Internode length*.—An average of 3 cm.

Foliage description:

*Leaf division*.—Simple.

*Leaf margins*.—Entire, bi-fid and trifid.

*Leaf size*.—Entire leaves; an average of 9.5 cm in length and 7 cm in width, trifid leaves; center lobe an average of 7 cm in length and 1 cm in width, lateral lobes an average of 4 cm in length and in 5 mm width.

*Leaf shape*.—Linear.

*Leaf base*.—Cuneate.

*Leaf apex*.—Acute.

*Leaf venation*.—Pinnate, inconspicuous, same color as leaf.

*Leaf attachment*.—Sessile.

*Leaf arrangement*.—Opposite.

*Leaf surface*.—Upper and lower surfaces; dull Upper and lower surfaces; dull and very sparsely to moderately covered with villous hairs at the base, up to 2 mm in length, NN155A in color.

*Leaf color*.—Young and mature upper surface; between 139A and 139B, lower surface; 139A.

Flower description:

*Inflorescence type*.—Composite with a single row of ray florets surrounding disc florets in the center, forming a radiant head, inflorescences are borne on branch terminals in loose corymbs.

*Lastingness of inflorescence*.—8 to 10 days until senescence of ray flowers, phyllarys and disc flowers are persistent.

*Fragrance*.—Mild citrus scent.

*Quantity of inflorescences*.—Free flowering, an average of 8 corymbs per main branch, an average of 4 composites per corymb.

*Inflorescence size*.—Corymbs; up to 20 cm in length and 14 cm in width, composite; an average of 2.5 cm in depth and 5 cm in diameter.

*Inflorescence buds*.—Globose and flattened in shape, an average of 4 mm in depth and 5 mm in diameter, dull surface; color; a blend of 137A and 138A.

*Peduncle*.—Rounded in shape, strong, an average of 10 cm in length and 2 mm in diameter, 139A in color, smooth and glabrous surface.

Phyllaries (involucral bracts):

*Phyllary number*.—2 rows; outer (lower) row 8, inner (upper) row 8.

*Phyllary arrangement*.—Outer (lower) phyllaries; 1% fused, pointing upward, inner (upper) phyllaries; surround receptacle with 30% of apical portion free, curved downward.

*Phyllary size*.—Outer (lower) phyllaries; an average of 8 mm in length and 1.5 mm in width, inner (upper) phyllaries; an average of 6 mm in length and 3 mm in width.

*Phyllary color*.—Upper and lower surfaces, outer (lower) phyllaries; 139A, base 139C, inner (upper) phyllaries; transluscent, 11A, base and center 139B.

*Phyllary texture*.—Outer (lower) phyllaries; glabrous and smooth on both surfaces, inner (upper) phyllaries; glabrous, slightly transluscent and slightly waxy on both surfaces.

*Phyllary apex*.—Acute.

*Phyllary base*.—Truncate.

*Phyllary shape*.—Outer (lower) phyllaries; elliptic, very slightly lanceolate, inner (upper) phyllaries; broadly lanceolate.

Ray florets (sterile):

*Number*.—8.

*Shape*.—Oblanceolate, with the appearance of 3 longitudinal sections.

*Size*.—An average of 2 cm in length and 1.3 cm in width.

*Apex*.—Rounded with notched and undulate lobes.

*Base*.—Cuneate.

*Margins*.—Entire and very slightly undulate.

*Aspect*.—Held mainly horizontal and slightly upwards, perpendicular to peduncle.

*Texture*.—Upper surface; satiny, velvety, glabrous and dull, lower surface; glabrous and dull.

*Color*.—Upper surface when opening and fully open; base 187A, center a blend of 59A and 187C, outer portion and margins 2A, lower surface when opening and fully open; 7A.

Disc florets (male and female):

*Number*.—An average of 120.

*Shape*.—Tubular, corolla is fused, flared and slightly curled at apex.

*Size*.—About 6 mm in length and 2 mm in width.

*Color*.—En masse; 22A, individual; corolla (tube) base and mid-section transluscent, 162D in color.

*Receptacle*.—An average of 8 mm in diameter and 5 mm in depth, 144A in color.

Reproductive organs:

*Presence*.—Disc flowers only.

*Gynoecium*.—1 Pistil; an average of 5 mm in length, style; very fine and 19B in color, bifid pillose, stigma; 22A in color with recurved branches about 0.4 mm in length, ovary is inferior, oblong in shape, an average of 2 mm in length and 1 mm in width, and 145C in color.

*Androecium*.—4 stamens, fused into tube surrounding style, an average of 3 mm in length and less than 0.5 mm in width, 200A in color, pollen; moderate in quantity and 22A in color.

*Seed*.—Seed development has not been observed, observed to be nearly sterile.

It is claimed:

1. A new and distinct cultivar of *Coreopsis* plant named 'Iron Lady' as herein illustrated and described.

* * * * *